(12) United States Patent
Dai

(10) Patent No.: US 12,227,731 B2
(45) Date of Patent: Feb. 18, 2025

(54) FLOW ELECTROPORATION DEVICE

(71) Applicant: Etta Biotech Co., Ltd., Suzhou (CN)

(72) Inventor: Edward Dai, Suzhou (CN)

(73) Assignee: ETTA BIOTECH CO., LTD., Suzhou (CN)

( * ) Notice: Subject to any disclaimer, the term of this patent is extended or adjusted under 35 U.S.C. 154(b) by 1129 days.

(21) Appl. No.: 16/756,269

(22) PCT Filed: Oct. 19, 2018

(86) PCT No.: PCT/CN2018/110915
§ 371 (c)(1),
(2) Date: Apr. 15, 2020

(87) PCT Pub. No.: WO2019/076353
PCT Pub. Date: Apr. 25, 2019

(65) Prior Publication Data
US 2020/0318055 A1    Oct. 8, 2020

(30) Foreign Application Priority Data

Oct. 19, 2017 (CN) .......................... 201710997572.5

(51) Int. Cl.
C12M 1/42    (2006.01)
C12M 1/34    (2006.01)
(Continued)

(52) U.S. Cl.
CPC ............ C12M 35/02 (2013.01); C12M 41/12 (2013.01); C12N 13/00 (2013.01); C12N 15/87 (2013.01); A61N 1/327 (2013.01)

(58) Field of Classification Search
CPC ...... C12M 35/02; C12M 35/04; C12M 41/12; C12M 23/16; C12M 23/12; C12M 25/02;
(Continued)

(56) References Cited

U.S. PATENT DOCUMENTS 6,090,617 A * 7/2000 Meserol ................. C12N 13/00
                                                      435/173.6
6,485,961 B1    11/2002 Meserol
(Continued)

FOREIGN PATENT DOCUMENTS

CA    2273880 A1    6/1998
CA    2997435 A1    3/2017
(Continued)

OTHER PUBLICATIONS

International Search Report issued Jan. 24, 2019 for PCT/CN2018/110915.
(Continued)

*Primary Examiner* — Michael L Hobbs
(74) *Attorney, Agent, or Firm* — Schmeiser, Olsen & Watts LLP

(57) ABSTRACT

Provided is a flow electroporation device, including a bracket and an electrode device, wherein the electrode device is planar electrode, and the bracket and the planar electrodes jointly restrict the channel for fluid flow; the material of the electrode device is one or several of following materials: titanium-plated platinum, platinum, rhodium-plated molybdenum, rhodium-plated ruthenium, iridium-plated niobium and platinum-plated iridium; the making process of the flow electroporation device is simple and the product can be manufactured in a standardized process. Compared to other similar devices, the single batch processing volume of cell suspension is larger, the transfection efficiency and the cell viability are higher, the stability is better, and the device is easy to operate.

14 Claims, 4 Drawing Sheets

(51) Int. Cl.
  *C12N 13/00* (2006.01)
  *C12N 15/87* (2006.01)
  *A61N 1/32* (2006.01)

(58) Field of Classification Search
  CPC .............. C12N 15/87; C12N 15/8207; C12N 15/8206; C12N 13/00; A61N 1/327; A61N 1/306; A61K 48/00; A61K 38/00; G01N 33/48728; H03K 3/57
  See application file for complete search history.

(56) References Cited

U.S. PATENT DOCUMENTS

| | | | |
|---|---|---|---|
| 6,617,154 | B1 | 9/2003 | Meserol |
| 7,678,564 | B2 * | 3/2010 | Muller-Hartmann ........................ C12M 35/02 435/283.1 |
| 2005/0282200 | A1 * | 12/2005 | Dzekunov .............. C12M 35/02 435/6.12 |
| 2012/0318726 | A1 * | 12/2012 | Charest .................. C12M 25/00 210/321.6 |
| 2016/0298074 | A1 | 10/2016 | Dai |
| 2018/0258379 | A1 | 9/2018 | Zahn et al. |

FOREIGN PATENT DOCUMENTS

| | | | | |
|---|---|---|---|---|
| CN | 101928666 | A | 12/2010 | |
| CN | 102174387 | A | 9/2011 | |
| CN | 103555574 | A | 2/2014 | |
| CN | 103865794 | A | 6/2014 | |
| CN | 103937669 | A | 7/2014 | |
| CN | 109153956 | A | 1/2019 | |
| EP | 3 070 158 | A1 | 9/2016 | |
| JP | 2007-295922 | A | 11/2007 | |
| JP | 4910716 | B2 | 4/2012 | |
| JP | 2018-529333 | A | 10/2018 | |
| KR | 10-2018-0042422 | A | 4/2018 | |
| WO | 9824490 | A1 | 6/1998 | |
| WO | WO-0208748 | A2 * | 1/2002 | ....... G01N 33/48728 |
| WO | 2006037527 | A1 | 4/2006 | |
| WO | 2015067221 | A | 5/2015 | |
| WO | WO-2016161201 | A2 * | 10/2016 | ............. A61N 1/327 |
| WO | 2017040995 | A1 | 3/2017 | |

OTHER PUBLICATIONS

Supplemental Search Report issued Mar. 5, 2020 for PCT/CN2018/110915.

* cited by examiner

FLOW ELECTROPORATION DEVICE

CROSS-REFERENCE TO RELATED APPLICATIONS

II. THIS APPLICATION CLAIMS PRIORITY TO PCT APPLICATION NO. CT/CN2018/110915, HAVING A FILING DATE OF Oct. 19, 2018, WHICH IS BASED ON CHINESE APPLICATION NO. 201710997572.5, HAVING A FILING DATE OF Oct. 19, 2017, THE ENTIRE CONTENTS BOTH OF WHICH ARE HEREBY INCORPORATED BY REFERENCE.

FIELD OF TECHNOLOGY

The following relates to the field of electroporation, particularly to a flow electroporation device, the method and device for delivering flowing bioactive loading substances into a flowing viable cell by an electric field.

BACKGROUND

The electroporation phenomenon was discovered in the 1970's. Cells are treated by an electric field to introduce micropores which can automatically close without permanent damage. This discovery makes it possible to introduce bioactive substances into cells. Previous studies suggest that there are four phenomena that may function in electroporation. The first phenomenon is insulation breakdown which refers to the micropores/holes introducing ability of high electric field on cell membrane. Once the micropores are formed, bioactive can be loaded into cells. The second phenomenon is the insulation bunching effect that refers to the mutual self-attraction generated through stacking of vesicles in a uniform electric field. The third phenomenon is vesicle fusion which refers to a trend that the merging of the membrane of vesicle forming micropores by insulation breakdown with the vesicle at the insulation breakdown site in a short distance. The fourth phenomenon is a trend that cells are arranged in a straight line along one of their axes in the presence of a high-frequency electric field. Thus, in order to load and unload cell vesicles, the electroporation involves the applications in the rotation of vesicle for pre-positioning, vesicle perforation and dielectric constant of the vesicle.

Most of electroporation chambers which can be obtained in current technologies are designed to be used only in a static state. Limited by volume, static electroporation chambers are neither suitable for processing a large number of samples, nor using high voltage or repeated charging. In order to treat cells at large volumes, flow electroporation chamber is developed.

Flow electroporation refers to such a process, comprising: transfer of mixed suspensions of cell suspension and exogenous bioactive loading substances into a device consisting of a fluid chamber or a fluid channel; the fluid chamber or fluid channel is constituted by electrodes arranged along the side of the fluid chamber or fluid channel, configured to and enable mixed suspensions in the fluid chamber or fluid channel exposed to electric field effect suitable for electroporation; and a device for transferring electroporated cell suspension out of the device. This method is particularly effective for large-volume cells. Patent CN195997A disclosed a flow electroporation chamber, which utilizes elastically deformable material as channel for fluid flow, and deformation of elastic material can act as a part of buffer for increasing instantaneous pressure in the fluid flow channel, but it did not develop electrode suitable for flow electroporation, thus no product has been launched to market after the patent had been disclosed for nearly 20 years.

Generally, a device for flow electroporation comprises two planar electrodes, which allow cell suspension to flow though continuously and stably until the entire cell suspension is electroporated, and comprises an electroporation chamber equipped with electrodes and port, which allows cell suspension to be injected through. The electrodes are connected to the circuit capable of providing a high-voltage pulse. The high-voltage pulse is controlled by a computer controlling program. The flow electroporation system, which has already been developed, permits large-volume electroporation to introduce target molecules into cells and obtain viable cells. However, currently there is very few successfully commercialized flow electroporation device. One reason is low market demand, the other is low efficiency of electroporation and stability of product.

Conditions for flow electroporation vary depending on type of cell and type of molecule which are expected to be introduced into cells. For any specific kind of cell, there are optimal parameters including optimal voltage, pulse width, optimal time interval and pulse number. In the use of a flow electroporation device described in the field, the flow velocity of cell suspension between electrodes when passing through the electroporation chamber as well as the pulse frequency can both be selected in order to achieve the optimal electrical pulse number applied to a certain volume of cell suspension. For example, for a specific kind of cell, if the optimal pulse number applied on each cell is known to be 2 times, the volume passing through electroporation chamber is 1 ml, then the flow velocity will be set to be 1 ml per unit time, and the pulse number applied in each unit time will be 2. If the electroporation is provided in such a manner, in this example, each cell will be subjected to two pulses. However, fluid dynamics flow of cell suspension passing through electroporation chamber will lead to cells passing through the chamber and flowing between electrodes at different velocities. Due to higher flow velocity near the chamber wall than that far from the chamber wall, for the cells that flowing to the liquid flow center between electrodes, the time taken to pass the zone between electrodes will be shorter than the unit time, and the pulse number may be less than 2 times. The time of passing the zone between electrodes consumed by cells flowing near the chamber wall is longer than the unit time, so the pulse number may be more than 2 times. Because the optimal pulse number of each cell is 2 times in this example, it is obvious that not every single cell is subjected to the optimal pulse numbers, and therefore the overall electroporation effect of cell suspension is not optimal.

Optimal conditions of electroporation vary depending on the specific type of cells subjected to electroporation and the type of molecules expected to be introduced into cells by electroporation. It is possible to solve this problem by experiment. Concretely speaking, conditions of electroporation can be changed in an organized manner by using static electroporation chamber, and then optimal conditions determined in experiments are applied to flow electroporation system. This approach has two defects. First, a large amount of time will be consumed for static chamber electroporation of large numbers of samples, so cells subjected to static electroporation may change in the test. Second, this approach is utilized just because it is believed that optimal conditions of static chamber electroporation are the same as those of flow electroporation, but it is uncertain whether this is true or not.

It is expected that one cell sample is sufficient to determine optimal conditions for carrying out all electroporation using the same device. These conditions may be used to large-scale cell electroporation for clinical treatment or other purposes.

The cuvette is mainly in the form of a colorimetric cup inserted with metal electrodes and used for electroporation or electric fusion. Containers for this purpose are mostly small ones with closed bottom and opening top, and the inner space is formed by two pairs of side walls which are oppositely arranged in parallel. The function of the internal space is to receive cell suspension in which cells to be treated are suspended, by buffer solution or cell culture medium. This kind of colorimetric cup often comprises a pair of voltage-applying electrodes arranged near the bottom of a pair of oppositely-arranged side walls. During discharge, current flows through cell suspension between two electrodes and makes nucleic acid or other molecules introduced into cells or lead to cell fusion according to selected conditions. The electrodes are often made of metal, commercially available particularly aluminum. However, these widely known and commercially available colorimetric cups have a defect, that is, metal ions can be emitted into buffer solution during discharge and thereby produce undesired stimulation that results in cytotoxicity. For example, by utilizing an aluminum colorimetric cup, side effects such as cell toxicity could be caused by release of $Al^{3+}$ ions. In addition, colorimetric cups with metal electrodes will cause undesired precipitation, which occurs due to release of metal ions from electrodes. The precipitates may be metal hydroxides or the conjugate of metal ions and biomacromolecules in buffer solution. The last defect of aluminum colorimetric cup is that its resistance is reduced during discharge probably for the reason that the aluminum oxide layer with relatively high resistance peels off the surface of electrodes during operation.

Tentative improvement to electrode material has been made in prior art. For example, Patent No. CN03805811.1 disclosed an electrode made of plastic conductive synthetic material which is doped with at least one kind of conductive substance, and the total concentration of dopants in this plastic is 20-80% w/w. These dopants contain carbon fibers, graphite, carbon black and/or carbon nanotubes, and can effectively treat cells or cell derivatives by utilizing current. Patent CN201610044870.8 discloses an electrotransfection device for cells, and its electrodes are covered by a nanowire structure. These nanowires are selected from copper oxide nanowires, titanium dioxide nanowires, gold nanowires, silver nanowires, copper nanowires, titanium nanowires, iron nanowires, platinum nanowires, titanium-platinum alloy nanowires, iron oxide nanowires, tin oxide nanowires or metal coated silicon nanowires. The transfection voltage is lower than or equal to 10V. The microstructure of the electrode surface can increase local electric field strength by 3 to 4 orders of magnitude, but the electrotransfection device is only used in static electroporation for adherent cells.

According to researches, main technical problems existing in the current flow electrotransfection process are changes in pH value of solution around cathode due to electrolysis of water, formation of harmful substances caused by surface oxidation of anode electrode, elevated solution temperature caused by Joule effect of current, as well as changes in the electric field intensity and its distribution caused by matters such as bubbles generated by electrotransfection.

During research and development process of the flow electroporation chamber of the present invention, development of the electrode is the core content, in which the electrode material is especially critical. The electrode material is directly in contact with cell suspension, and an electrochemical reaction occurs in the electroporation process which causes changes in electric field and affects the results consequently. Meanwhile, unstable anode material would release metal ions that lead to cell death or contamination of cell suspension thus cause greater harm. Therefore, developing of stable electrode material with biocompatibility is the primary goal in this invention for achieving commercial application of flow electroporation.

In the flow electroporation chamber of the present invention, the electrodes are in contact with cell suspension in the electroporation process, and electrolysis reaction of water occurs on the surface of electrodes to produce bubbles. Ideally, these bubbles can be quickly discharged from the electroporation chamber along with the liquid flow. However, due to the influence of electrode structure and surface roughness of electrode material, these bubbles may be retained in the electroporation chamber, therefore the electric field intensity distribution changes because these bubbles are not electrical conductive; meanwhile, these bubbles occupy the chamber cavity and change the flow rate of solution, thus the number and intensity of current pulse received by cells flowing through the electrode zone changed and so are the electroporation results. Therefore, the present invention must solve the technical problems caused by bubbles produced during electroporation, and find a way to discharge these bubbles.

When cell suspension stably flows the electroporation chamber, high-voltage pulses are applied to cells. Heat is generated according to the Joule Law when high-voltage pulses are repeatedly applied on electrodes, which must be carried away by a cooling device to prevent the temperature of electrodes and cell suspension from reaching too high. Because the liquid flow in the flow electroporation chamber is stable and continuous, the electrodes are generating heat continuously, the measure to remove heat from the electroporation chamber must be effective to prevent the temperature of electroporation chamber from rising to an unacceptable degree. Therefore, keeping the temperature in flow electroporation chamber and temperature of planar electrodes within a controllable range is also a technical goal of present invention.

Due to the difference between cross-sectional areas of catheter and electroporation chamber, the instant pressure change will occur when the fluid enters the electroporation chamber. Maintaining the stability of the flow velocity of liquid crossing sections in order to stabilize flow velocity and pulse number is also a technical problem to be solved by the invention.

SUMMARY

An aspect relates to improved electrodes for a flow electroporation device, that would replace aluminium electrodes to increase electrotransfection efficiency and cell viability.

Another aspect of the invention is to provide a flow electroporation device, which allows liquid to flow through the electroporation chamber at a relatively constant velocity.

Another aspect of the invention is to provide a flow electroporation device, which reduces the formation of bubbles and improves discharge of bubbles, by optimizing the structure of electrode and the controlling system of electric field, thus prevent retention of bubbles on electrodes from affecting electrotransfection results.

Another aspect of the invention is to provide a flow electroporation device, which can effectively maintain temperature of planar electrodes within a certain range during electrotransfection.

Another aspect of the invention is to provide a method of making the flow electroporation device, which takes simple steps, is easy to operate, and enables standardized production.

Another aspect of the invention is to provide an example of application of the flow electroporation device for large volume cell electrotransfection.

Another aspect of the invention is to provide a flow electroporation system, which controls its grounding environment.

A flow electroporation device, comprising a bracket and an electrode device, is characterized in that the electrode device consists of planar electrodes, and the bracket and the planar electrodes jointly restrict the channel for fluid flow; preferably, the planar electrodes are in flat shape, smooth on surface, and in contact with the bracket smoothly and tightly;

Material of the planar electrodes is one or several of platinum-plated titanium, platinum, molybdenum-plated rhodium, ruthenium-plated rhodium, niobium-plated iridium and iridium-plated platinum.

Preferably, the planar electrodes are fixed on the bracket of the flow electroporation device. Medical-grade plastic is selected as the material for the bracket. The flow electroporation device further comprises a flow inlet and a flow outlet connecting to the channel.

Preferably, the flow electroporation device further comprises a power supply, with which the electrode device is electrically connected.

Preferably, the surface of the planar electrode substrate material can be coated or plated, and the coating or plating material could be different from the substrate material; Preferably, coating or plating material of the planar electrodes could be one or several of gold, silver, titanium, iridium oxide, iridium, platinum, niobium, ruthenium, molybdenum, rhodium, tungsten and conductive ceramic. Preferably, the planar electrode material could be one or several of following materials: gold-plated platinum, silver-plated platinum, iridium-plated platinum, niobium-plated platinum, ruthenium-plated platinum, molybdenum-plated platinum, rhodium-plated platinum and conductive ceramic-plated platinum. Preferably, the planar electrode material could be one or several of following materials: gold-plated titanium, silver-plated titanium, iridium-plated titanium, platinum-plated titanium, niobium-plated titanium, ruthenium-plated titanium, molybdenum-plated titanium, rhodium-plated titanium and conductive ceramic-plated titanium. Preferably, the planar electrode material could be one or several of following materials: gold-plated iridium, silver-plated iridium, platinum-plated iridium, niobium-plated iridium, ruthenium-plated iridium, molybdenum-plated iridium, rhodium-plated iridium and conductive ceramic-plated iridium. Preferably, the planar electrode material could be one or several of following materials: gold-plated rhodium, silver-plated rhodium, iridium-plated rhodium, platinum-plated rhodium, niobium-plated rhodium, ruthenium-plated rhodium, molybdenum-plated rhodium and conductive ceramic-plated rhodium.

Preferably, the thickness of plating on the planar electrodes is 0.1-10 μm.

The flow electroporation device of the present invention primarily comprises a bracket and planar electrodes defining the channel for fluid flow. Two pieces of planar electrodes are embedded into the bracket in parallel and form an electroporation chamber. The planar electrodes comprise a device electrically connected to a high-voltage pulse power supply. Two pieces of planar electrodes are respectively connected to positive and negative poles of output electric signals of the high-voltage pulse power supply. After the electric signals are connected, a uniform electric field is formed in the electroporation chamber between the two planar electrodes, thus the fluid flowing along the flow channel and passing through the electroporation chamber is subject to a pulsed electric field.

Metal materials with good electric conductivity are selected to make the flow electroporation electrode of the invention. These materials are also required to possess stable electrochemical properties to avoid chemical reaction with the cell solution during electroporation process and prevent the formation of harmful substances.

Materials available to be used electrode substrate include aluminum, stainless steel, gold, silver, titanium, platinum, iridium, niobium, ruthenium, rhodium, molybdenum, tungsten, conductive ceramic and the like. Preferably, the electrode material could be one or several of following materials: gold, titanium, platinum, iridium, niobium, ruthenium, molybdenum, tungsten and rhodium.

Further preferably, the shape of the planar electrodes is one or several of followings: parallelogram, circle and oval.

Further preferably, the shape of the planar electrodes is a right-angled parallelogram. Further preferably, the shape of the planar electrodes is rectangular.

Further preferably, the length of the planar electrodes is not shorter than 8 mm, and not longer than 25 mm.

Further preferably, the length of the planar electrodes is 8 mm.

Further preferably, the length of the planar electrodes is 12.5 mm.

Further preferably, the length of the planar electrodes is 15 mm.

Further preferably, the length of the planar electrodes is 25 mm.

Further preferably, the width of the planar electrodes is not shorter than 2 mm, and not longer than 10 mm.

Further preferably, the width of the planar electrodes is 2 mm.

Further preferably, the width of the planar electrodes is 4 mm.

Further preferably, the width of the planar electrodes is 10 mm.

Further preferably, the length of the planar electrodes is 15 mm, and the width is 10 mm.

Further preferably, the thickness of the planar electrodes is not less than 0.1 mm, and not more than 5 mm.

Further preferably, the thickness of the planar electrodes is not less than 0.5 mm.

Further preferably, the thickness of the planar electrodes is not less than 1 mm, and not more than 3 mm.

Further preferably, the thickness of the planar electrodes is 2 mm.

Further preferably, the surface area of the planar electrodes is not smaller than 10 $mm^2$, and not larger than 2500 $mm^2$.

Further preferably, the surface area of the planar electrodes is not smaller than 50 $mm^2$, and not larger than 1000 $mm^2$.

Further preferably, the two planar electrodes are made of the same material or different materials.

Further preferably, the distance between the two planar electrodes is not less than 0.5 mm, and not more than 8 mm.

Further preferably, the distance between the two planar electrodes is not less than 1 mm, and not larger than 5 mm.

Preferably, the flow electroporation device further comprises a catheter which is fixedly connected to the bracket and comprises a liquid inlet tube connected to the flow inlet and a liquid outlet tube connected to the flow outlet. The fluid flows into the chamber through the liquid inlet, electroporated under the action of the electric field, and finally flows out of the liquid outlet.

Further preferably, the diameter of the liquid outlet tube is not smaller than that of the liquid inlet tube.

Preferably, the diameter of the catheter is not smaller than 2 mm, and not larger than 10 mm. Preferably, the catheter is made of medical grade plastic or medical grade silicone. Further preferably, the connection mode of the catheter and the bracket includes but is not limited to threaded connection, snap connection, cladded connection and ultrasonic welding.

Further preferably, the liquid inlet tube and the liquid outlet tube are in a straight-line shape.

Further preferably, the angle between the axis direction of the flow inlet and the length direction of the channel ranges within 0-90°.

Further preferably, the angle between the axis direction of the flow outlet and the length direction of the channel ranges within 0-90°.

The flow direction of fluid flowing into and out of the electroporation chamber could be one of the two directions: in parallel flow direction or in vertical flow direction of the fluid flowing through the electroporation chamber.

Further preferably, the axis direction of the flow inlet is parallel to the length direction of the channel.

Further preferably, the axis direction of the flow outlet is parallel to the length direction of the channel.

Preferably, at least one fluid buffer zone is set on the bracket. The fluid buffer zone could locate between the flow inlet and the electrodes, and/or between the flow outlet and the electrodes. Further preferably, the shape of cross section of the fluid buffer zone could be, but not limited to, triangle, regular trapezoid, inverted trapezoid, square, semicircle, semi-oval, arc and S-shape.

Preferably, the flow electroporation device further comprises a fluid driving device, which drives the fluid in positive pressure and/or negative pressure mode.

Preferably, the fluid driving device is a peristaltic pump or a magnetic pump.

Further preferably, the fluid driving device drives the fluid in a negative pressure mode.

Further preferably, the flow electroporation device further comprises a cooling and temperature control device including a temperature control and cooling module for cooling the electrode device.

Further preferably, the temperature control and cooling module is attached to the outer sides of the planar electrodes.

Further preferably, the cooling and temperature control device uses one of following measures: cooling liquid, cooling gas, cooling tube, cooling fin and cooling fan.

Preferably, the flow electroporation device further comprises an electric pulse generating device and a control system.

Preferably, the flow electroporation device further comprises at least one fluid storage device.

Preferably, the flow electroporation device further comprises a temperature regulating device for regulating the ambient temperature of the flow electroporation device.

Further preferably, the temperature regulating device controls the ambient temperature of the flow electroporation device within 0-40° C.

Preferably, the flow electroporation device further comprises a carbon dioxide generating and regulating device for adjusting the concentration of carbon dioxide in the ambient environment of the flow electroporation device. Further preferably, the carbon dioxide generating and regulating device controls the carbon dioxide in the ambient environment of the flow electroporation device within 3-8%.

The present invention further provides a flow electroporation device for transfecting bioactive loading substances and non-bioactive loading substances into cells. The bioactive and non-bioactive loading substances respectively comprise bioactive molecules and non-bioactive molecules. The flow electroporation device is any one of the flow electroporation devices described in the application.

Further preferably, the bioactive substance includes but is not limited to medicaments, gene loading substances such as DNA and RNA, cytokines, antibodies or other proteins.

Further preferably, the non-bioactive substance includes cell growth factors and contrast agent nanoparticles.

Preferably, the type of cell includes but is not limited to prokaryotic cells, eukaryotic cells and plant protoplasts.

Further preferably, the prokaryotic cells comprise bacteria, fungi and saccharomyces. Further preferably, the eukaryotic cells comprise animal derived cell lines, primary cells and egg cells.

Preferably, the flow inlet is located at the bottom part of the flow electroporation device, and the flow outlet is located at the upper part of the flow electroporation device.

The invention further provides a method for making the flow electroporation device, including following steps:

The bracket with a flow inlet and a flow outlet is fabricated by injection molding or Computerized Numerical Control (CNC) or 3D printing technology, and the bracket has two recessed windows; A metal layer is coated on the surface of metal substrate of the planar electrodes by electroplating or coating, and the material of the planar electrodes is selected from one or several of followings: platinum-plated titanium, platinum, molybdenum-plated rhodium, ruthenium-plated rhodium, niobium-plated iridium and iridium-plated platinum;

The two planar electrodes are mounted onto the two recessed windows, and then the planar electrodes are encapsulated.

Preferably, the method of coating or plating of planar electrodes is coating or electroplating, and the preparation process comprises these steps: prior treatment, pretreatment, coating or electroplating and drying.

Prior treatment comprises selection of proper substrate for shape processing, surface treatment by sand blasting, selection of different sand blasting meshes according to the thickness of coating, and cleaning the surface oxidation layer by acid pickling.

Pretreatment comprises ultrasonic cleaning by using a cleaning agent and washing with deionized water to remove residuals of the cleaning agent.

Coating is soaking, brushing or spraying/coating with the spray gun, then dry to form a uniform coating layer on the substrate surface. Electroplating is plating a uniform coating on the surface of substrate by electrolysis. Wash with deionized water after coating or electroplating, removing coating or electroplating solution and dry for use.

The invention further provides a method using the flow electroporation device for electrotransfection. Cells and loading substances are added into a solution (such as electroporation buffer), which is then transferred to the flow electroporation device where the loading substances are transfected into cells. The flow electroporation device comprises:

power supply, bracket, electrode device, electric pulse generating device and control system, and the bracket comprises a channel for fluid flow, and a flow inlet and a flow outlet connected to the channel; the electrode device is electrically connected to the power supply and located in the channel, and the material of the electrode device includes one or several of following materials: platinum-plated titanium, platinum, molybdenum-plated rhodium, ruthenium-plated rhodium, niobium-plated iridium and iridium-plated platinum;

A voltage is applied to the planar electrodes, which generate a current with the density as high as 120 $A/cm^2$, and the bioactive loading substances are transferred into cells as the result of electroporation.

A voltage is applied to the electrodes, which generate a current, and the density of the current is 2-14 $A/cm^2$.

Preferably, the pulse width of the current is 0.01-100 ms.

A voltage is applied to the electrodes to generate an electric field in the channel, and the field intensity of the voltage is 0.2-10 kV/cm.

Wherein, the pulse width of the current is 0.01-100 ms.

Compared with the conventional art, the flow electroporation device of the invention has achieved significant progress and unexpected better technical effects:

Planar electrodes made of materials preferably selected by the invention can provide a continuous and stable current and provide a stable and uniform electric field in buffer solution, thus significantly improve the electroporation efficiency and ensure high cell viability;

When the preferably selected planar electrodes of the invention were placed in buffer solution, even while a high pulse voltage was applied, it showed unexpectedly that the electrolysis reaction was very mild and few bubbles were formed, these created favorable conditions for continuously applying pulses to planar electrodes;

Very little $OH^-$ (cathode effect) was generated by the planar electrodes of the invention during operation, so pH values of cell suspension was not changed. Therefore, the damage caused to cells is mild and the cell viability is high;

The flow electroporation device of the invention could be manufactured in a standardized process. Compared to other products, the volume of cell suspension for a single batch of the flow electroporation device of present invention is larger, the transfection efficiency and cell viability are higher, the stability is better and the device is easier to operate. For the cells electroporated by the flow electroporation device of the invention, the electrotransfection efficiency and the cell viability are both higher than 60% for all cell types. By optimizing the inlet and outlet structure in the bracket, the mixed cell suspension and bioactive loading substance can uniformly enter the electroporation chamber, and the cells treated by electric shock and other substances generated during the electrotransfection process can be discharged from the electroporation chamber smoothly. The flow electroporation device of the invention can be used for processing large volume cell suspension, and it significantly improve the electrotransfection efficiency while remarkably increase cell viability. The flow electroporation device of the invention is an advanced flow electroporation product, which can be used for electrotransfection in laboratory and antibody drug R&D, thus have great potential for commercialization.

A BRIEF DESCRIPTION OF THE DRAWINGS

FIG. 1 graphically depicts current stability of aluminium electrodes of different sizes;

FIG. 2 graphically depicts current stability of conductive ceramic coated titanium electrodes, aluminium electrode and gold-plated stainless-steel electrode;

Note: 1—catheter (liquid outlet tube); 2—liquid outlet of bracket; 3—first buffer zone; 4—electroporation chamber; 5—first planar electrodes; 6—first planar electrodes cooling device; 7—catheter (liquid inlet tube); 8—liquid inlet bracket; 9—second buffer zone; 10—bracket; 11—second planar electrodes cooling device; 12—second planar electrodes; 13—cooling liquid inlet; 14—cooling liquid outlet; 15—cooling liquid inlet; 16—cooling liquid outlet.

DETAILED DESCRIPTION

The implementation plan of embodiments of the present invention will be described in detail with reference to the specific embodiments, and it is understandable to technicians in the field that following embodiments only illustrate embodiments of the invention, and are not considered to restrict the scope of embodiments of the invention. The conditions not noted in the embodiments should be set according to the conventional conditions in the field or those recommended by the manufacturer.

Embodiment 1

Selection of Shape and Size of Electrode

The flow electroporation device of embodiments of the invention adopts planar electrodes, whose size determines the amount of cell to be processed within a unit time, while the length, width and distance of the electroporation chamber have different effects on fluid flow, respectively. The length of planar electrodes affects the duration of solution flow in electrodes at a constant flow velocity. An increase of electrode length can prolong the duration of bubbles attached to electrode surface when flow through the electroporation chamber, thus increase the probability of bubble retention. The width of planar electrodes affects the flow velocity of solution in the electroporation chamber, more specifically, the flow velocity in the middle zone of fluid is faster and that in the periphery zone is slower, and the larger the width of electrodes is, the larger the difference would be. The distance between planar electrodes affects the strength of the electric field, and according to the formula $E=U/d$, under the same voltage, the larger the distance is, the weaker the electric field would be. When increasing electrode distance, the output voltage of the instrument must be increased to achieve an optimal electric field strength for electrotransfection.

Figure 1:
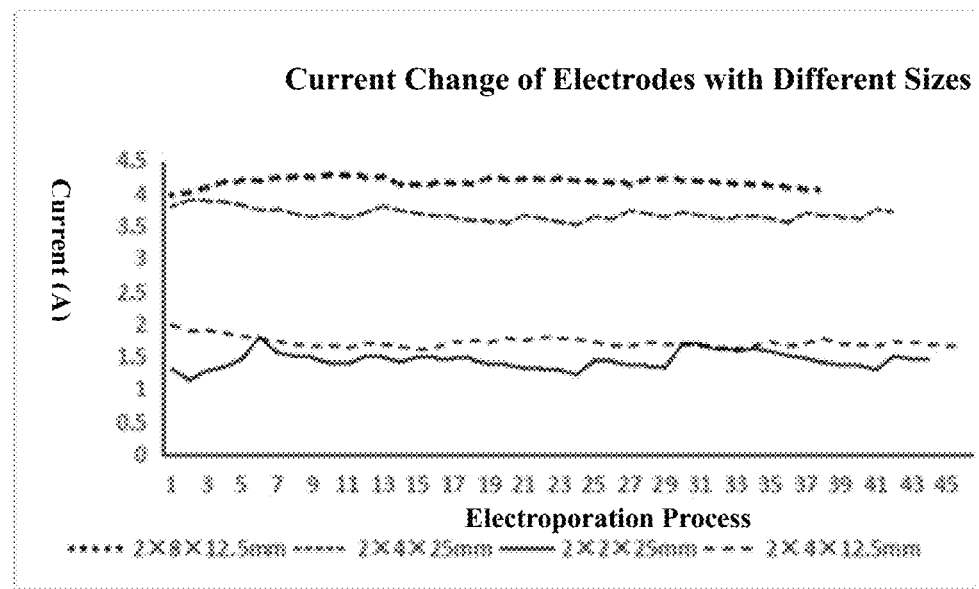

Experimental design: planar electrodes with different ratios of lengths and widths are used in manufacture of the flow electroporation device; changes of current data tested by using an empty buffer solution and observe the formation and discharge of bubbles, thereby, optimize the ratio of length and width of planar electrodes. The shape of planar electrodes is selected to be rectangular or square. Aluminum is selected as the testing material for planar electrode. The length, width and thickness of the test sample are set to: 15×10×2 mm, 25×4×2 mm, 25×2×2 mm and 12.5×4×2 mm, respectively. The bracket with two recessed windows is manufactured by CNC or 3D printing, and the size of the recessed windows is identical to that of the planar electrodes described above. Planar electrodes are embedded into recessed windows, and then the bracket is encapsulated to form an electroporation chamber with a fluid flow inlet and a fluid flow outlet. The two electrodes of the device are connected to the positive and negative poles at the output end of the pulse power supply, respectively. The electrotransfection parameter is 150 V for voltage, 11 ms for pulse length, and shock 1 time. Add a corresponding volume of EL buffer solution (sold by Suzhou Etta Biotech and its agents, article number: H10305), record the change of current data during electroporation process (see FIG. 1), and observe the formation and discharge of bubbles in the whole process. Testing results of electroporation: for electrodes with a length of 25 mm, small bubbles formed during electroporation process were likely to accumulate on the surface of electrodes, gradually grow into large bubbles and then discharged, thus caused periodic fluctuation of current and reduced stability of electric field. For electrodes with a length of 12.5 mm, small bubbles formed during electroporation process were discharged along with the solution flow and seldom accumulate on electrodes, so the current stability is better. However, the total volume of electroporation chamber with planar electrodes of 2×4 mm is only half of that for 2×8 mm electrodes, so 2×8 mm was selected under the same condition to increase the processing capacity within a unit time. When the length of electrodes and the distance between electrodes remain unchanged, if the width of electrodes was changed separately, the larger the width of electrodes is, the larger the processing quantity within a unit time would be, and vice versa. However, when increasing the width, the difference in flow velocities between solution in the side zone and the middle zone of electrodes will become larger. Therefore, 15×10×2 mm is an optimal electrode size.

Embodiment 2

Selection of Planar Electrode Material

For the flow electroporation device of embodiments of the invention, R&D of planar electrode material is the core issue. The surface of planar electrodes should be smooth and flat and planar electrodes should be mounted to the bracket smoothly and tightly to form a sealed chamber, to reduce the possibility of bubble retention as much as possible. By selecting a good electrode material, optimizing electrode structures and controlling electric field intensity, the adverse effects of electrochemical reaction products on electrotransfection during electroporation process could be alleviated.

Experimental design: The planar electrode material available for selection in the preferred embodiment includes aluminum, 304 stainless steel, pure gold, gold plated-stainless steel, pure titanium, conductive ceramic coated titanium, pure platinum, platinum-plated titanium and pure iridium;

- Aluminum: widely used as an electrode material in the field of electrotransfection;
- 304 stainless steel: excellent bio-affinity, low cost and is the most common medical grade metal material;
- Gold-plated-stainless steel: Gold is a metal material with stable chemical and conductive properties and excellent biocompatibility;
- Pure titanium: a metal material with excellent biocompatibility and wide application in the field of biomedicine;
- Conductive ceramic coated titanium: provided by Professor Xin from Soochow University, the coating material is conductive ceramics and is with excellent antioxidation property;
- Platinum-plated titanium: a stable anode material, widely applied in the electrolysis industry and with excellent biocompatibility;
- Pure gold: extremely high anti-corrosion stability, good conductivity and thermal conductivity, extremely easy to process and form, and easily to be plated to the surface of other metal, ceramics and glass;
- Pure platinum: extremely stable chemical properties, insoluble in strong acid and alkali solutions, with catalytic activity and able to be used as material for anti-cancer drug.
- Pure iridium: very stable chemical properties, insoluble in aqua regia, and widely applied in high-tech fields, such as aerospace technology, pharmacy and automobile industry.

The materials above are made into planar electrodes with length×width×thickness of 15×10×2 mm. Similar to the first embodiment, a bracket with two recessed windows is manufactured by CNC or 3D printing, and the size of the recessed windows is identical to that of the planar electrodes described above. Planar electrodes made of the materials above are mounted into the recessed windows, and then the bracket is encapsulated to form an electroporation chamber with a fluid flow inlet and a fluid flow outlet. The two electrodes embedded in the bracket are connected to the positive and negative poles at the output ends of the pulsed power supply, respectively, to form an electroporation device.

In the first test, an empty buffer solution (refer to no cells and bioactive loading substances exist in the buffer solution) was used, and conductive ceramic coated titanium planar electrodes, aluminium electrodes, gold-plated stainless steel electrodes, pure titanium electrodes and platinum-plated titanium electrodes were selected, and setting the electrotransfection parameters was 150 V voltage, 11 ms pulse width, 1 time electric shock and 2352 ms interval. The stability of assembled electrodes were tested by electric shock tests with 30 ml of electrotransfection buffer, the data of current during electroporation process were recorded (the experiment results were shown in FIG. 2.), an observation was made to the change of color of solution after electrotransfection (FIGS. 3-7), and that of planar electrode surface (FIGS. 8-12).

Figure 2:
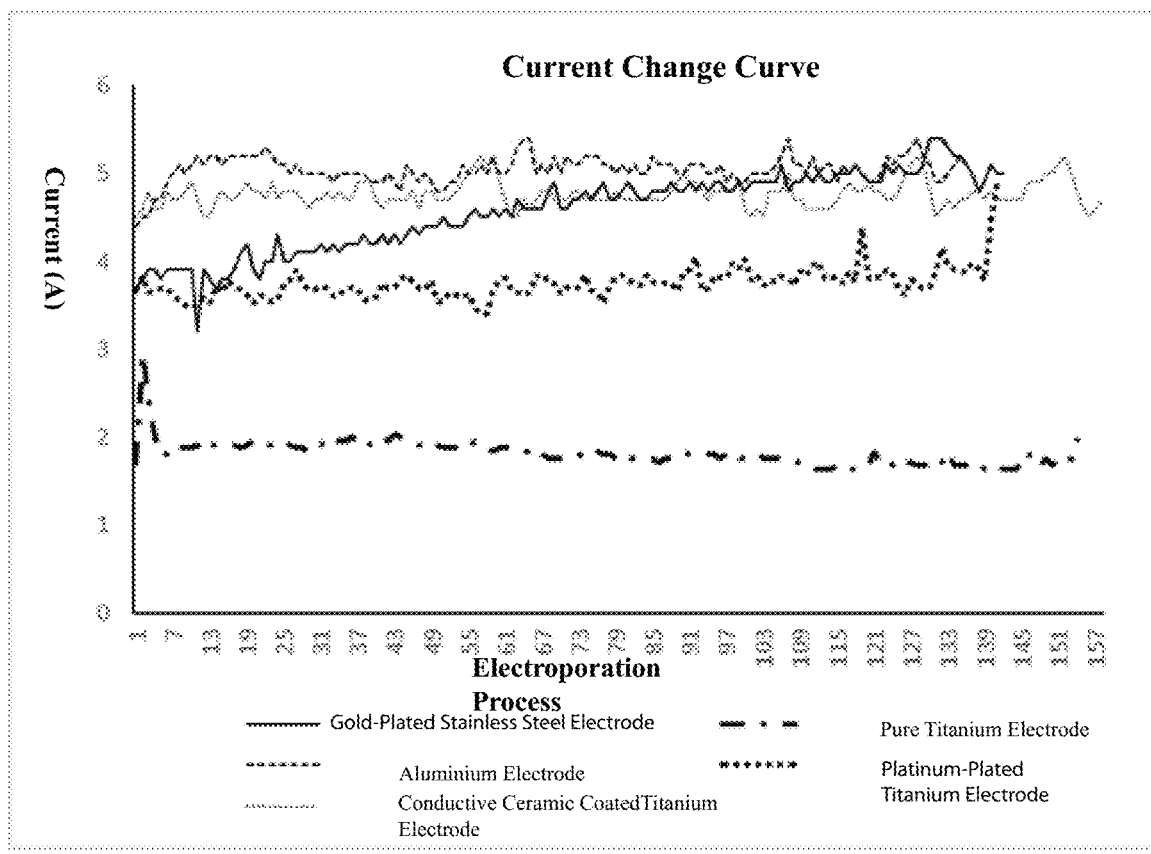
Figure 3:
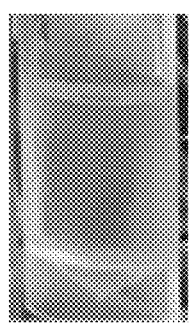
FIG. 3 depicts a color change of solution after electrotransfection using titanium planar electrodes with conductive ceramic coating.

As observed from FIG. 2, the current of gold-plated stainless steel electrodes gradually increases from 4 A to 5 A; the current of aluminium electrodes rapidly increases from 4.5 A to 5 A and then fluctuates around 5 A; and the current of conductive ceramic coated titanium planar electrodes is very stable all the time and keeps at 4.8 A. The currents of conductive ceramic coated titanium electrodes, aluminium electrodes and platinum-plated titanium electrodes are relatively stable, the current of gold-plated stainless steel electrodes gradually increases, and the current of pure titanium electrodes decreases at the beginning, then slowly increases and tends to be stable later, meanwhile, the current waveform changes.

Changes of the color of solutions after electroporation with various materials are shown in FIGS. 3-7. Conductive ceramic coated titanium planar electrodes can react with chloride ions in the solution, and the solution turns yellow (FIG. 3) after electroporation. The released ion can influence the cell viability after electrotransfection, and no apparent precipitate is generated after centrifugation.

Figure 4:
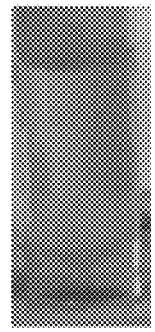
FIG. 4 depicts a color change of solution after electrotransfection using aluminium electrodes.
Figure 5:
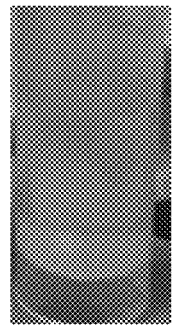
FIG. 5 depicts a color change of solution after electrotransfection using gold-plated stainless-steel electrodes.

During electroporation process, for aluminium and gold-plated stainless steel, a violent oxidation reaction occurs to anode. $Al^{3+}$ from aluminium electrodes reacts with $OH^-$ in the solution to generate white precipitates (FIG. 4). Therefore, aluminum cannot be used as an anode material because the generated oxides will fall into cell suspension. The gold fall from the surface of gold-plated stainless steel electrodes (FIG. 10) and the solution becomes slightly yellow (FIG. 5).

White foams are generated from all of the three materials mentioned above, mostly from the aluminium electrodes which have white precipitates (FIG. 4).

Figure 6:
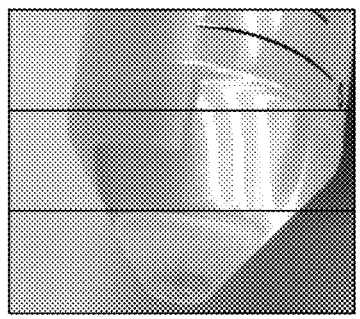
FIG. 6 is a color of solution after electrotransfection using pure titanium electrodes.

After electric shock using pure titanium planar electrodes, no color change occurs to the solution, but there is visible particle precipitation after centrifugation, and the precipitate exists in the whole process (FIG. 6).

Figure 7:
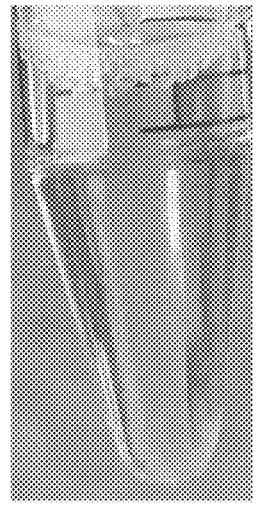
FIG. 7 is a color of solution after electrotransfection using platinum-plated titanium electrodes.
Figures 8, 9:
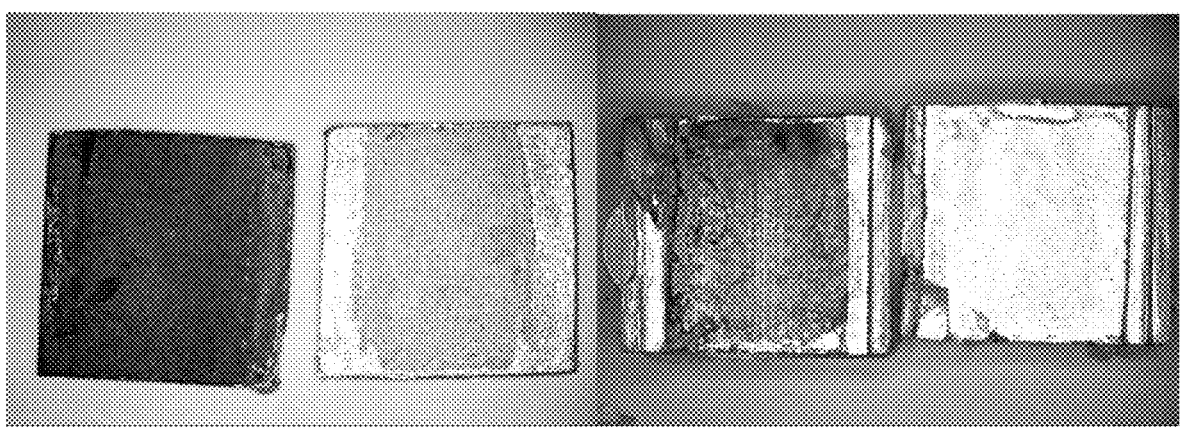
FIG. 8 depicts a change on surface of conductive ceramic coated titanium planar electrodes after electrotransfection (anode on the left and cathode on the right)
FIG. 9 depicts a change in a surface of aluminium electrodes after electrotransfection (anode on the left and cathode on the right)
Figure 10:
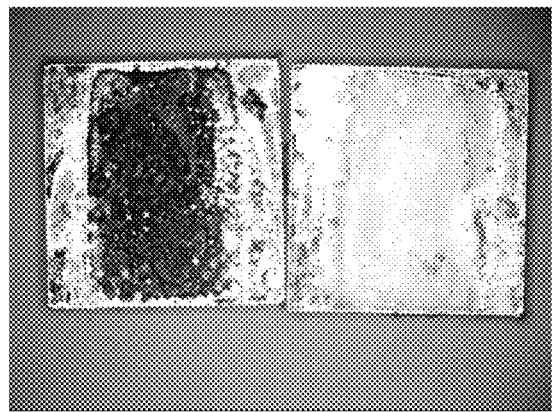
FIG. 10 depicts a change in a surface of gold-plated stainless-steel electrodes after electrotransfection (anode on the left and cathode on the right)
Figure 11:
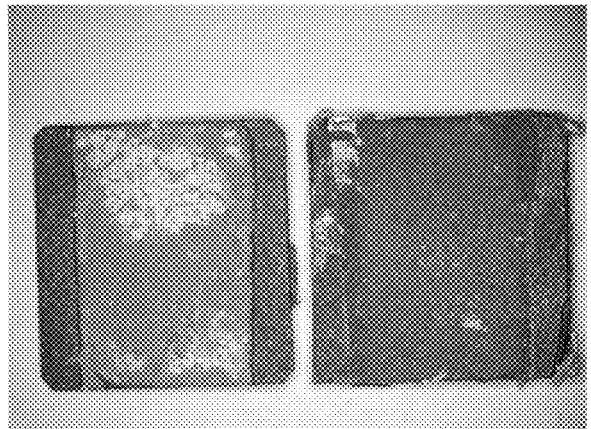
FIG. 11 depicts a change in a surface of pure titanium electrodes after electrotransfection (anode on the left and cathode on the right)
Figure 12:
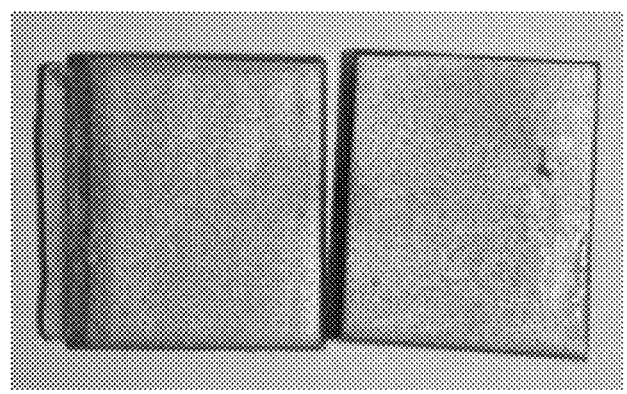
FIG. 12 depicts a change on a surface of platinum-plated titanium electrodes after electrotransfection of (anode on the left and cathode on the right)

After electric shock using platinum-plated titanium planar electrodes, no color change occurs to the solution, no precipitate is visible, and no precipitate after centrifugation (FIG. 7). After electroporation, the electrodes are dismantled. As observed from FIGS. 8-12, the surface of conductive ceramic coated titanium planar electrodes is not oxidized (FIG. 8), but aluminium electrodes (FIG. 9) and gold-plated stainless steel planar electrodes are oxidized, and in particular, the gold-plating layer of the gold-plated stainless steel planar electrodes peeled off (FIG. 10). Pure titanium electrodes are oxidized to form an oxide layer (FIG. 11), and the surface of platinum-plated titanium electrodes is not oxidized (FIG. 12).

In the second test, fluid containing pMAX plasmid (purchased from Lonza Human T cell Nucleofector® Kit, article number: VAPA-1002), CHO-S cells (donated by Professor Zhou from Peking University Health Science Center, who purchased from Life Technology™, article number: R80007) and EL Buffer is injected into the electroporation chamber from the bottom of the electroporation device mentioned above, and then electroporated. In the test, different electrode materials are selected and the parametres are set to 150V voltage, 11 ms pulse width, 1 time electric shock and an interval of 2352 ms, or 150V voltage, 5 ms pulse width, 3 times electric shock and an interval of 784 ms. After electroporation, the fluid flows out from outlet on the top, cells are cultured, and electrotransfection efficiency and cell viability are measured.

TABLE 1

Experiment results of electrotransfection of cells by conductive ceramic coated titanium electrodes, aluminium electrodes, gold-plated stainless-steel electrodes and pure titanium electrodes under parametres of 150 V/11 ms/1 time

| Electrode Type | TE | VE | MIX | MFI |
| --- | --- | --- | --- | --- |
| Gold-plated stainless-steel electrodes | 29.66% ± 2.26% | 43.74% ± 15.43% | 12.97% ± 4.57% | 8.74E+05 ± 3.64E+05 |
| Aluminium electrodes | 33.35% ± 2.64% | 31.78% ± 3.94% | 10.59% ± 1.75% | 3.86E+06 ± 9.68E+05 |
| Conductive ceramic coated titanium electrodes | 39.98% ± 2.67% | 59.06% ± 14.24% | 23.55% ± 5.44% | 2.75E+06 ± 3.64E+05 |
| Pure titanium electrodes | 44.02% ± 3.30% | 71.83% ± 5.74% | 31.64% ± 2.13% | 2.10E+06 ± 1.67E+05 |

Note:
TE: transfection efficiency;
VE: cell viability;
MIX: comprehensive efficiency;
MFI: mean fluorescence intensity The electrotransfection results of the four electrode materials show that, for 30 ml volume, the transfection efficiency remains almost unchanged, with a fluctuation of about 5%. TE: pure titanium>conductive ceramic coated titanium>aluminum>gold-plated stainless steel; VE: pure titanium>conductive ceramic coated titanium>gold-plated stainless steel>aluminum; MIX: pure titanium>conductive ceramic coated titanium>aluminum=gold-plated stainless steel; MFI: pure titanium>aluminum>conductive ceramic coated titanium>gold-plated stainless steel

TABLE 2

Experiment results of electroporation of cells by conductive ceramic coated titanium electrodes and titanium-plated platinum electrodes under parametres of 150 V/5 ms/3 times

| Electrode Type | TE | VE | MIX | MFI |
|---|---|---|---|---|
| Conductive ceramic coated titanium electrodes | 56.74% ± 8.97% | 53.73% ± 13.73% | 30.48% ± 9.19% | 6.35E+06 ± 4.61E+05 |
| Titanium-plated platinum electrodes | 67.08% ± 8.87% | 67.32% ± 10.9% | 45.15% ± 5.4% | 6.49E+06 ± 6.21E+05 |

Platinum-plated titanium electrodes and conductive ceramic coated titanium electrodes have little difference in TE, but VE of the former is 15% higher than that of the latter. Their MFIs are almost consistent, but MIX of the former is higher than that of the latter.

Although the electrotransfection result of pure titanium electrodes is superior to that of aluminium and gold-plated stainless steel electrodes, the anode of pure titanium electrodes can be oxidized, the stability of electric field may change and black substance peeling off is observed in the solution after electrotransfection, so pure titanium is not suitable to be used as an anode material. The electrotransfection solution of conductive ceramic coated titanium electrodes turns yellow. TEs of platinum-plated titanium electrodes and conductive ceramic coated titanium electrodes are close to each other, but VE of the former is higher, so MIX of the former is higher than that of the latter.

Embodiment 3

Selection of Different Methods for Fluid Entering/Exiting Electroporation Chamber Experiment design: the angle between horizon and the angle at which fluid enters the electroporation chamber and flows in the electroporation chamber can range between 0° and 90°. When the angle is 0°, the fluid flows straight in and straight out; when the angle is 90°, the fluid flows side in and side out. The mode of fluid straight-in-straight-out is that the liquid inlet and outlet of the bracket extend in a straight line, so the silicone tube at the near end of electrodes are in the same direction with electrodes. The mode of fluid side-in-side-out is that the liquid inlet and outlet of the bracket is in a 90° angle with planar electrodes, so the silicone tubes at the near end of electrodes are in vertical direction with electrodes.

Figure 13:
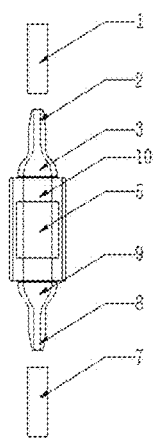
FIG. 13 depicts a schematic diagram of a straight-in-straight-out mode of the fluid.
Figure 14:
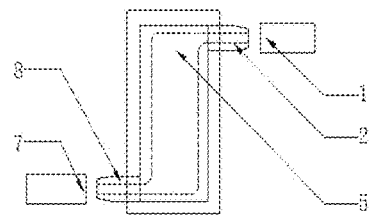
FIG. 14 depicts a schematic diagram of a side-in-side-out mode of the fluid.

Platinum-plated titanium planar electrodes are selected for testing the straight-in-straight \-out (FIG. 13) and side-in-side-out mode (FIG. 14) of fluid in electroporation experiment described above, in which CHO-S cell is electrotransfected with pMAX plasmid. Under the parametres of 150 V voltage, 11 ms pulse width, 1 time electric shock and interval of 2352 ms, and 150V voltage, 5 ms pulse width, 3 times electric shock and interval of 784 ms, the difference in stability of the two types of planar electrodes in the electrotransfection process is compared by monitoring the stability of current in the electrotansfection process and the formation and discharge of bubble masses (mixture of bubbles and dead cells); meanwhile, the difference of electrotransfection result of the two types of electrodes is compared by testing transfection efficiency (TE), cell viability (VE) and mean fluorescence intensity (MFI) etc. in different time intervals.

TABLE 3

Electrotransfection effect of straight-in- straight-out and side-in-side-out modes under the parametres of 150 V/11 ms/1 time

| Type | Current | TE | VE | MIX | MFI |
|---|---|---|---|---|---|
| Forward-in-forward-out | 4.89 ± 0.11 | 42.86% ± 6.39% | 70.77% ± 4.89% | 30.37% ± 4.99% | 8.86E+06 ± 1.82E+06 |
| Side-in-side-out | 4.91 ± 0.12 | 39.87% ± 18.23% | 73.45% ± 5.23% | 29.28% ± 5.02% | 7.95E+06 ± 1.76E+06 |

TABLE 4

Electrotransfection results of straight-in-straight-out and side-in-side-out modes under the parametres of 150 V/5 ms/3 times

| Type | Current | TE | VE | MIX | MFI |
|---|---|---|---|---|---|
| Forward-in-forward-out | 4.74 ± 0.16 | 68.45% ± 6.27% | 55.45% ± 14.99% | 37.95% ± 7.81% | 7.87E+06 ± 6.39E+05 |
| Side-in-side-out | 4.65 ± 0.17 | 68.06% ± 16.49% | 60.18% ± 14.56% | 40.95% ± 7.41% | 7.80E+06 ± 1.35E+06 |

It can be observed from the average value and the standard deviation of current measurement that: the current stabilities of electrodes in straight-in-straight-out and side-in-side-out modes are both excellent. It can be observed from the result values of cell electrotransfection that: there is little difference of the two electrodes in TE, VE and MIX between straight-in-straight-out and side-in-side-out modes, but MFI of positive cells in straight-in-straight-out mode is higher than that in side-in-side-out mode.

| Shape of Buffer zone | Current | TE | VE | MIX | MFI |
| --- | --- | --- | --- | --- | --- |
| Cone | 4.74 ± 0.16 | 68.45% ± 6.27% | 55.45% ± 14.99% | 37.95% ± 7.81% | 7.87E+06 ± 6.39E+05 |
| Square | 3.75 ± 0.89 | 47.52% ± 13.29% | 64.69% ± 15.32% | 30.74% ± 11.53% | 6.71E+06 ± 3.87E+05 |
| Arc | 4.82 ± 0.14 | 69.73% ± 5.61% | 58.25% ± 8.64% | 40.61% ± 6.89% | 8.25E+06 ± 4.55E+05 |
| Trapezoid | 4.61 ± 0.21 | 58.47% ± 7.02% | 62.48% ± 9.15% | 36.53% ± 7.96% | 7.52E+06 ± 6.68E+05 |

The principal difference between straight-in-straight-out and side-in-side-out modes in the inverted-U-shaped collection pipeline system is only in corner angle at the outlet end of electrodes. The corner angle in side-in-side-out mode is 90°, and the bubble masses stay for long and accumulate in large quantities at the corner. The corner angle in straight-in-straight-out mode is larger than 90° due to the radian of silicone tube, so stay and accumulation of bubble masses are alleviated and the electrotransfection efficiency at each section is improved as compared with the side-in-side-out electrodes.

There is not obvious difference in strength and stability of electric field and electrotransfection results between straight-in-straight-out and side-in-side-out modes, but the straight-in-straight-out mode is easier for discharge of bubbles, so electrotransfection results and stability in this mode are better.

Embodiment 4

Setup of Fluid Buffer Zone

If the cross section of the liquid inlet of bracket is circular but that of planar electrode chamber is square, a retention zone would easily generate due to the direct change from circular to square. The flow velocity of solution in the retention zone is zero, so it is an ineffective electrotransfection zone in which bubbles are likely to accumulate. Therefore, a buffer zone needs to be added between the liquid inlet and the planar electrode area for a smooth transition and avoiding retention zone to ensure a stable flow velocity of solution in the planar electrode area. Theoretically, the larger the buffer zone is, the more stable the flow velocity in the electrode area would be. Similarly, a buffer zone is also needed to be added between the planar electrode area and the liquid outlet of the bracket to avoid quick closing and impact on flow velocity by the change in pressure. A gradual increase in pressure in the buffer zone makes bubbles generated in electrolysis are likely to accumulate on the tube wall when they flow through. If bubbles cannot be discharged in time and the volume of them gradually increases, the effect of the buffer zone is counteracted thereby the effect of stabilizing the flow velocity cannot be achieved. In this case, the shape of the buffer zone needs to be considered. Firstly, the inner pressure of the solution can be increased so that bubbles are easily discharged. Secondly, no retention zone should be generated at the corner. Finally, the transition should be smooth and the pressure in the solution should not be violently changed.

Figure 15:
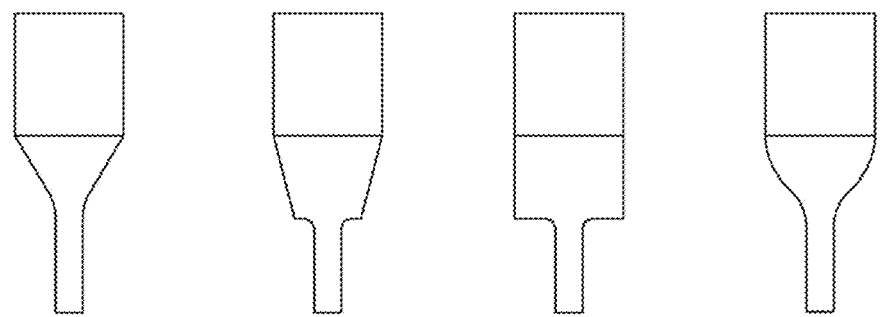
FIG. 15 depicts a structural diagram of the buffer zone.

Experiment design: Platinum-plated titanium planar electrodes are selected. Buffer zones for fluid are arranged at the top and the bottom of the straight-in-straight-out electroporation chamber respectively (FIG. 13) to overcome the change of instantaneous pressure intensity when the fluid enters the electroporation chamber from the liquid inlet of the bracket. The shapes of the buffer zone are set to cone, square, arc and trapezoid (FIG. 15).

The experiment results indicate that: the electroporation device with conical buffer zone has less accumulated bubbles at the liquid outlet, and residual bubbles are mostly accumulated in the right-angle position of the inner edge of electrodes; the electroporation device with square buffer zone accumulates a large amount of bubbles at the liquid outlet and discharges at a time when accumulated to a certain amount, so the liquid flow is not uniform; the electroporation device with arc buffer zone accumulates least bubbles, the current is the most stable and the transfection efficiency is the highest; and the bubble accumulation and transfection efficiency with trapezoidal buffer zone is moderate.

Embodiment 5

Fluid Driven by Positive or Negative Pressure

The flow electroporation device drives the fluid flow by positive and/or negative pressure, preferably by negative pressure. The rotation of peristaltic pump is used as the power to drive fluid flow, so the fluid enters the electroporation chamber for electrotransfection, and cells after electrotransfection and other substances generated during electrotransfection are brought out of the electroporation chamber to ensure electrotransfection efficiency. Depending on the position of the peristaltic pump, two modes of liquid driving power are available, namely positive pressure and negative pressure. The positive pressure mode is to place the peristaltic pump on the front side of the electroporation chamber, while the liquid is pushed by the thrust generated by the rotating peristaltic pump to unidirectionally flow in the pipeline system and into the electroporation chamber. The negative pressure mode is to place the peristaltic pump on the back side of the electroporation chamber, the suction force generated by rotating the peristaltic pump is used for extracting samples in the sample tube and enabling them to flow in the pipeline system unidirectionally through the electroporation chamber.

Experiment design: the electroporation device with a straight-in-straight-out arc buffer zone is used to monitor current stability in the process with two fluid driving modes. The formation and discharge of bubble masses during electroporation process under the two modes of positive pressure and negative pressure were observed, and the electric field intensity and the flowing stability of the fluid in the pipeline compared. The CHO-S cell electrotransfection with pMAX performed under the two modes, with the parametres of 150 V voltage, 5 ms pulse width, 3 times electric shock and an interval of 784 ms. Platinum-plated titanium planar electrodes are selected, the TE, VE, MIX and MFI of cells are obtained, and then the electrotransfection results and stability of cells under the two modes are compared

TABLE 6

Cell electrotransfection results under positive and negative pressure modes

| Type | Current | TE | VE | MIX | MFI |
|---|---|---|---|---|---|
| Positive pressure | 5.20 ± 0.39 | 64.86% ± 13.35% | 50.81% ± 8.00% | 32.39% ± 6.44% | 2.85E+06 ± 4.02E+05 |
| Negative pressure | 4.95 ± 0.55 | 76.14% ± 10.86% | 56.25% ± 7.19% | 42.80% ± 7.08% | 5.85E+06 ± 1.10E+06 |

Result analysis: it can be observed from the average measured current and the standard deviation that: the electric field intensity is consistent under the two modes of positive pressure and negative pressure; in CHO-S cell electrotransfection, the current is 5.20±0.39A in the positive-pressure mode and 4.95±0.55A in the negative pressure mode, the difference between them is small and the stability is good.

It can be observed from the motion of fluid and bubble masses in the pipeline system that, the formation and discharge of bubble masses on the electrode surface are almost the same and reflect as the formation of small-volume bubble masses form first, are discharged quickly without retention, and concentrate to become large bubble masses at the joint of electrodes and bracket. Then slow down and concentrate to become even larger bubble masses at the outlet end of electrodes, and finally enter the collection pipeline system. However, the discharge of bubble masses in the collection pipeline has a relatively big difference: under the positive pressure condition, bubble masses are prone to stay and accumulate at the corner of the pipeline, and when sampling is carried out by sections, no bubble masses can be collected from the front section, but a large number of bubble masses are collected from the rear section, so that flow velocity in the electrotransfection process is not uniform, and the volume of cell saps collected at different sections is not uniform. Under the negative pressure condition, fewer bubble masses stay and accumulate at the corner of the pipeline; for sample taking by sections, the distribution of bubble masses and the volume of cell saps in the collection pipeline are consistent. Compared with positive pressure, under the negative pressure mode, the transportation of the fluid suspension in the pipeline is more stable, and the discharge of bubble masses is more uniform and smoother.

It can be observed from the cell electrotransfection results that: TE, VE, MIX and MFI of cell electrotransfection under the negative-pressure mode are higher than those under the positive-pressure mode. TE and VE are more stable under the negative-pressure power mode, which can effectively promote the flow and discharge of bubble masses in the pipeline system. Then, the sample tube can be vertically placed, so that the phenomena of liquid leakage caused by poor sealing of the sample tube can be avoided, and meanwhile, it facilitates the modification of the sample feeding pipeline system in the later period.

Embodiment 6

Cooling and Temperature Control Device of Planar Electrodes

Figure 16:
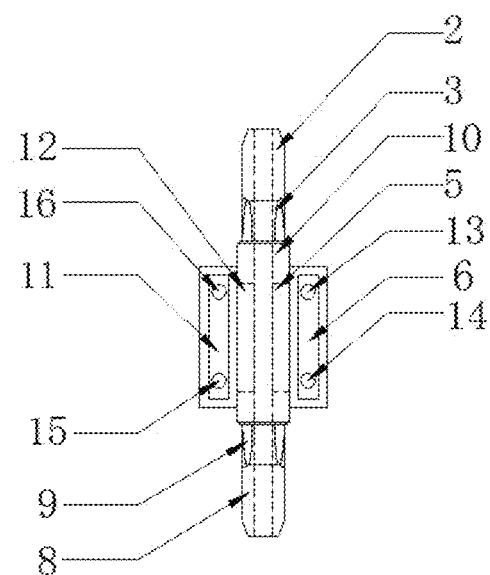
FIG. 16 depicts a schematic diagram of an electrode cooling temperature control device for cooling and controlling the temperature of electrodes.
Figure 17:
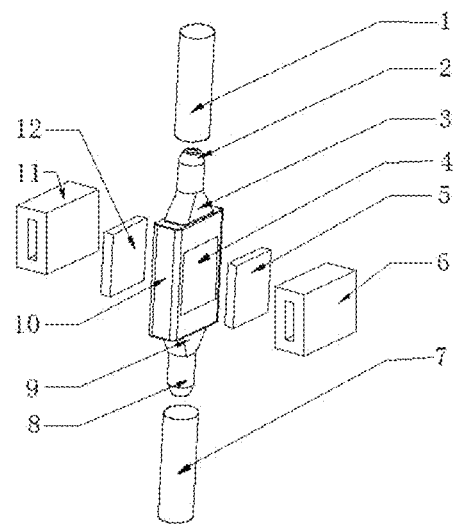
FIG. 17 depicts an overall structure of the device.

A cooling and temperature control device is attached at the outer side of planar electrodes (FIG. 16), and the temperature control and cooling module is adhered to the outer side of planar electrodes by heat conducting glue and it is internally provided with a cooling tube which is connected to the circulating pump and the semiconductor colling chip; the circulating pump drives the cooling liquid in the cooling pipe to take away heat which is transmitted to the cooling module by planar electrodes and keep temperature stability of planar electrodes; and the semiconductor cooling chip is used for cooling the cooling liquid flowing back from the cooling module.

Experiment design: the same cells and experiment conditions as the second embodiment are adopted, planar electrodes with a cooling and temperature control device and titanium planar electrodes with conductive ceramic coating but without a cooling and temperature control device are used for comparison experiments of cell transfection.

Experiment results: the monitoring results of the temperature of working planar electrodes show that: during electrotransfection process, the planar electrodes with a cooling device has little temperature change on outer surface, and the average temperature is 38.6° C.±2.3° C., which is on average 9.5° C. lower than those without a cooling device, TE is 9.3% higher and VE is 11.2% higher.

Embodiment 7

Comparison Between Single-Tube Liquid Entry and Continuous Liquid Entry

Single-tube liquid entry means that the peristaltic pump pushes cell suspension to enter and fill electroporation chamber and then stops working temporarily until cell suspension in the electroporation chamber has been electroporated, then continue and push new cell suspension to enter and fill the electroporation chamber, i.e. repeating the steps of liquid entry-stop-electric shock; continuous liquid entry means that the peristaltic pump works continuously and pushes cell suspension to continuously pass through the electroporation chamber, and pulsed power supply applies an electric field to cell suspensions at the designed frequency to perform electroporation. Experiment design: According to the experiment results from the second embodiment to the sixth embodiment, the optimal experiment conditions are selected. Conductive ceramic coated titanium electrodes are selected, the distance between electrodes is 1.5 mm, and the size of electrode that has contact with solution is 4 mm×8 mm. The structures of the liquid inlet and the liquid outlet of the bracket are straight-in-straight-out and side-in-side-out, respectively. A fluid buffer zone is arranged on the straight-in-straight-out bracket, the liquid outlet is directly planarly transitioned to a 2 mm round hole, and the peristaltic mode of continuous liquid entry at negative pressure is used. The validation tests are carried out in a stable electrotransfection system: EL buffer, voltage of 150 V, pulse width of 5 ms, 3 times, an interval of 784 ms, 5 E+06 cell/ml, pMAX plasmid of 20 μg/ml, and electrotransfection volume of 10 ml. The single-tube liquid entry and the continuous liquid entry modes are compared under multiple electrotransfection conditions to compare the current stability and the formation and elimination of bubbles. TE, VE, MIX and MFI are obtained in tests in which pMAX plasmid is transfected into CHO-S cells under the two work modes, so as to compare the electrotransfection results and stability of cells in the two liquid entry modes.

TABLE 7

Electrotransfection results and current change of single-tube liquid entry and continuous liquid entry using conductive ceramic coated titanium electrodes

| Type | TE | VE | Mix | MFI | Current |
|---|---|---|---|---|---|
| Straight-in-straight-out single-tube liquid entry | 37.65% ± 12.50% | 59.92% ± 9.15% | 22.55% ± 5.62% | 8.80E+06 ± 4.73E+05 | 4.76 A ± 0.29 |
| Straight-in-straight-out continuous liquid entry | 58.45% ± 15.63% | 55.45% ± 14.99% | 32.41% ± 7.81% | 7.26E+06 ± 6.39E+05 | 4.74 A ± 0.12 |
| Side-in-side-out single-tube liquid entry | 43.04% ± 5.88% | 56.56% ± 6.59% | 24.34% ± 2.56% | 8.48E+07 ± 7.63E+05 | 4.63 A ± 0.25 |
| Side-in-side-out continuous liquid entry | 52.39% ± 25.17% | 55.16% ± 22.24% | 28.89% ± 13.36% | 7.80E+06 ± 1.35E+06 | 4.65 A ± 0.17 |

The current monitoring results show that under the electrotransfection condition of 150 V/5 ms/3 times, the average current of single-tube liquid entry and continuous liquid entry are almost consistent, but due to single-tube liquid entry, bubbles generated in three times of electric shock are accumulated and then discharged in one time, resulting in decreased current stability and increased error values. The results of cell electrotransfection show that continuous liquid entry is much better than single-tube liquid entry. In both straight-in-straight-out and side-in-side-out structures of electrodes, continuous liquid entry has better results than single-tube liquid entry.

Embodiment 8

Electroporation Experiment of Different Electrode Materials under Optimal Conditions Experiment design: the aluminum, conductive ceramic coated titanium, gold-plated stainless steel, titanium, gold, iridium, rhodium, niobium, ruthenium, molybdenum, tungsten, platinum-plated titanium and platinum are selected as materials for planar electrodes. Among them, conductive ceramic coated titanium is provided by the Physical Material Laboratory of Soochow University; titanium, gold, platinum-plated titanium and platinum are purchased from Beijing NovElite Co, Ltd.; aluminum and gold-plated stainless steel are purchased from Beijing Goodwill Metal Technology Co., Ltd.; and iridium, rhodium, niobium, ruthenium, molybdenum and tungsten are supplied by Xiamen Tungsten Group. The distance between the electrodes is 1.5 mm, and the size of the electrode that is in contact with solution is 4 mm×8 mm. The structure of the liquid inlet and the liquid outlet of the bracket is straight-in-straight-out, the bracket has a fluid buffer zone, the liquid outlet is directly planarly transitioned to a 2 mm round hole, and the peristaltic mode of continuous liquid entry at negative pressure is used. The validation tests are carried out in a stable electrotransfection system: EL buffer, voltage of 150 V, pulse width of 5 ms, 3 times, an interval of 784 ms, 1.00 E+07 cells/ml, pMAX plasmid of 20 µg/ml, and electrotransfection volume of 40 ml.

TABLE 8

Electrotransfection results of different flow electroporation electrodes

| Type of Electrode Material | TE | VE | MIX | MFI |
|---|---|---|---|---|
| Aluminum | 50.15% ± 2.18% | 44.69% ± 3.94% | 22.41% ± 1.97% | 3.67E+06 ± 5.48E+05 |
| Conductive ceramic coated titanium | 59.97% ± 3.78% | 66.44% ± 8.96% | 39.84% ± 5.65% | 2.75E+06 ± 2.57E+05 |
| Gold-plated Stainless-steel | 44.49% ± 2.85% | 52.48% ± 12.26% | 23.34% ± 3.67% | 9.64E+05 ± 2.84E+05 |
| Titanium | 66.03% ± 3.19% | 74.93% ± 4.62% | 49.47% ± 3.41% | 2.80E+06 ± 1.52E+05 |
| Gold | 77.59% ± 11.80% | 64.05% ± 7.59% | 49.25% ± 1.67% | 7.18E+06 ± 2.50E+06 |
| Iridium | 66.79% ± 3.56% | 59.21% ± 5.98% | 39.54% ± 2.33% | 4.62E+06 ± 2.54E+05 |
| Rhodium | 66.37% ± 3.25% | 63.83% ± 11.92% | 42.36% ± 4.21% | 4.79E+06 ± 2.63E+05 |
| Niobium | 58.55% ± 2.63% | 57.82% ± 10.05% | 33.85% ± 3.74% | 7.85E+05 ± 2.41E+05 |
| Ruthenium | 67.80% ± 3.28% | 73.46% ± 4.35% | 49.80% ± 3.21% | 3.61E+06 ± 1.02E+05 |
| Molybdenum | 71.55% ± 9.33% | 76.84% ± 5.47% | 54.97% ± 2.16% | 8.85E+06 ± 2.69E+06 |
| Platinum | 86.93% ± 5.33% | 63.55% ± 1.08% | 55.24% ± 2.9% | 6.03E+06 ± 7.13E+05 |
| Tungsten | 54.75% ± 5.16% | 69.70% ± 3.42% | 38.16% ± 2.33% | 3.23E+06 ± 1.12E+05 |
| Titanium-plated gold | 78.74% ± 9.13% | 69.45% ± 5.35% | 54.68% ± 3.82% | 6.98E+06 ± 2.76E+06 |

TABLE 8-continued

Electrotransfection results of different flow electroporation electrodes

| Type of Electrode Material | TE | VE | MIX | MFI |
|---|---|---|---|---|
| Platinum-plated iridium | 85.43% ± 6.21% | 79.66% ± 5.36% | 68.05% ± 3.45% | 7.89E+06 ± 2.33E+05 |
| Iridium-plated rhodium | 77.92% ± 5.11% | 70.87% ± 6.75% | 55.22% ± 3.44% | 5.69E+06 ± 2.31E+05 |
| Titanium-plated platinum | 92.25% ± 0.78% | 90.65% ± 0.21% | 83.62% ± 0.9% | 6.69 + 06 ± 2.23E+05 |
| Iridium-plated niobium | 83.56% ± 3.98% | 79.63% ± 8.25% | 66.53% ± 2.76% | 7.24E+05 ± 2.16E+05 |
| Rhodium-plated ruthenium | 85.47% ± 3.99% | 80.12% ± 4.74% | 68.47% ± 3.85% | 7.55E+06 ± 2.37E+05 |
| Rhodium-plated molybdenum | 86.79% ± 8.63% | 78.34% ± 3.51% | 67.99% ± 3.01% | 8.06E+06 ± 2.13E+06 |

Based on comparison of experiment data between Table 8 and Tables 1-2, the comprehensive efficiency of the flow electroporation device of the present invention under optimized conditions is remarkably improved in comparison with the initial simple flow electroporation device.

For aluminium electrodes, under the same electrotransfection conditions, the transfection efficiency is 50.15%; white salt is precipitated out in the solution resulting in cytotoxicity, and the cell viability is 44.69%;

For conductive ceramic coated titanium electrodes, under the same electrotransfection conditions, the transfection efficiency is 59.97%; The solution turns slightly yellow, results in slight cytotoxicity, and the cell viability is 59.06%;

For gold-plated stainless steel, the transfection efficiency is 44.49% and the cell viability is 52.48%; in the electrotransfection process, the gold peels off, the solution turns yellow and the electrode oxidation is noticeable;

For titanium electrodes, in the electrotransfection process, the transfection efficiency and the cell viability are higher than those with conductive ceramics, reaching 66.03% and 74.93%, respectively; however, after centrifuging the solution after electrotransfection, it is observed that substances peel off to form precipitates;

For gold electrodes, under the same electrotransfection conditions, the transfection efficiency is 77.59% and the cell viability is 64.05%; no color change is observed in the solution, no precipitate is separated out, and the electrode piece with gold as anode is extremely easy to be oxidized in the electrotransfection process;

Iridium, rhodium, niobium, ruthenium, molybdenum and tungsten electrodes are relatively stable. No significant changes occur to the solution and electrode surface after electrotransfection. The transfection efficiency and the cell viability ranged 58-71% and 57-76%, respectively, and the comprehensive efficiency is superior to that of aluminium electrodes and gold-plated stainless steel electrodes.

For platinum electrodes, under the same electrotransfection conditions, the transfection efficiency is 86.93%, the cell viability is 63.55%; no color change and peeling are observed in the solution during electrotransfection, and no change occurs to anode and cathode of electrodes after electrotransfection, so the stability is good.

For titanium-plated platinum electrodes, the transfection efficiency and cell viability can reach 92.25% and 90.65% respectively, which are much higher than those using electrodes made of other materials; no color change and precipitate are observed in the solution, so the stability is excellent.

Gold-plated titanium, iridium-plated platinum, rhodium-plated iridium, niobium-plated iridium, ruthenium-plated rhodium and molybdenum-plated rhodium are stable and oxidation-resisting, therefore achieve very good results. Transfection efficiency and cell viability were within 77-86% and 69-80%, respectively. Overall efficiency is high and can meet the actual needs of flow electroporation.

Although the present invention has been disclosed in the form of preferred embodiments and variations thereon, it will be understood that numerous additional modifications and variations could be made thereto without departing from the scope of the invention.

For the sake of clarity, it is to be understood that the use of 'a' or 'an' throughout this application does not exclude a plurality, and 'comprising' does not exclude other steps or elements.

The invention claimed is:

1. A flow electroporation device comprising:
a bracket;
an electrode device including planar electrodes for subjecting an electric field to flowing viable cells therebetween, the flowing viable cells not being cancer cells, wherein the bracket and the planar electrodes jointly restrict a channel for fluid flow;
wherein a material of the planar electrodes comprises one or more of platinum-plated titanium, molybdenum-plated rhodium, ruthenium-plated rhodium, niobium-plated iridium and iridium-plated platinum;
wherein the bracket has recessed windows, and the planar electrodes are mounted in the recessed windows and encapsulated.

2. The flow electroporation device according to claim 1, further comprising a flow inlet connected to the channel and a flow outlet connected to the channel.

3. The flow electroporation device according to claim 1, wherein a thickness of a plating of the planar electrodes is 0.1-10 μm.

4. The flow electroporation device according to claim 1, wherein a length of the planar electrodes is not shorter than 8 mm and not longer than 25 mm, and/or, a width of the planar electrodes is not shorter than 2 mm and not longer than 10 mm.

5. The flow electroporation device according to claim 1, wherein a thickness of the planar electrodes is not smaller than 0.1 mm and not larger than 5 mm.

6. The flow electroporation device according to claim 1, wherein a distance between the planar electrodes is not less than 0.5 mm and not larger than 8 mm.

7. The flow electroporation device according to claim 2, further comprising a catheter which is fixedly connected to the bracket, and the catheter comprises a liquid inlet tube connected to the flow inlet, and the catheter further comprises a liquid outlet tube connected to the flow outlet.

8. The flow electroporation device according to claim 7, wherein a diameter of the liquid outlet tube is not smaller than a diameter of the liquid inlet tube.

9. The flow electroporation device according to claim 2, wherein an angle between an axis direction of the flow inlet and a length direction of the channel ranges within 0-90°, and/or, an angle between an axis direction of the flow outlet and the length direction of the channel ranges within 0-90°.

10. The flow electroporation device according to claim 2, wherein at least one fluid buffer zone is arranged on the bracket, and the at least one fluid buffer zone is located between the flow inlet and the planar electrodes, and/or, the at least one fluid buffer zone is located between the flow outlet and the planar electrodes.

11. The flow electroporation device according to claim 1, further comprising at least one fluid storage device.

12. The flow electroporation device according to claim 2, wherein the flow inlet is located at a bottom side of the flow electroporation device, and the flow outlet is located at an upper side of the flow electroporation device.

13. A method for making a flow electroporation device, the method comprising:

fabricating a bracket with a flow inlet and a flow outlet by injection molding, Computerized Numerical Control or 3D printing technology, wherein the bracket has two recessed windows;

fabricating an electrode device using planar electrodes, wherein the flow electroporation device comprises:
the bracket;
the electrode device includes the planar electrodes for subjecting an electric field to flowing viable cells therebetween, the flowing viable cells not being cancer cells, wherein the bracket and the planar electrodes jointly restrict a channel for fluid flow;
wherein a material of the planar electrodes comprises one or more of platinum-plated titanium, molybdenum-plated rhodium, ruthenium-plated rhodium, niobium-plated iridium and iridium-plated platinum;
wherein the bracket has recessed windows, and the planar electrodes are mounted in the recessed windows and encapsulated.

14. A method comprising:
utilizing a flow electroporation device, wherein cells and loading substances are added into a solution, and the solution is then transferred to the flow electroporation device, further wherein the loading substances are transferred into the cells,
wherein the flow electroporation device comprises:
a bracket;
an electrode device including planar electrodes for subjecting an electric field to flowing viable cells therebetween, the flowing viable cells not being cancer cells, wherein the bracket and the planar electrodes jointly restrict a channel for fluid flow;
wherein a material of the planar electrodes comprises one or more of platinum-plated titanium, molybdenum-plated rhodium, ruthenium-plated rhodium, niobium-plated iridium and iridium-plated platinum;
wherein the bracket has recessed windows, and the planar electrodes are mounted in the recessed windows and encapsulated;
wherein, a voltage is applied to the electrode device, and an electric field is generated in the channel, and a field intensity of the electric field is 0.2-10 kV/cm.

* * * * *